United States Patent
Lehtinen et al.

(10) Patent No.: US 6,551,833 B1
(45) Date of Patent: Apr. 22, 2003

(54) METHOD FOR HANDLING SAMPLES AND DIAGNOSTIC MEASURING DEVICE

(75) Inventors: Kauko Lehtinen, Raisio (FI); Tom Javen, Kaarina (FI); Vesa Sonne, Turku (FI); Aarne Heinonen, Turku (FI); Mika Routamaa, Lieto (FI)

(73) Assignee: Innotrac Diagnostics Oy, Turku (FI)

( * ) Notice: Subject to any disclaimer, the term of this patent is extended or adjusted under 35 U.S.C. 154(b) by 0 days.

(21) Appl. No.: 09/523,517

(22) Filed: Mar. 10, 2000

(30) Foreign Application Priority Data

Mar. 12, 1999 (FI) .................................................. 990559

(51) Int. Cl.[7] ............................................. G01N 35/04
(52) U.S. Cl. .............................. 436/48; 436/43; 436/45; 436/47; 436/49; 436/54; 436/164; 436/180; 422/63; 422/64; 422/65; 422/82.05; 422/100; 198/349.5; 198/349.6; 198/465.2
(58) Field of Search .......................... 422/63–65, 82.05, 422/100; 436/43, 45, 47–49, 54, 164, 180; 198/349.5–349.6, 465.2

(56) References Cited

U.S. PATENT DOCUMENTS

| | | | | |
|---|---|---|---|---|
| 4,476,733 A | * | 10/1984 | Chlosta et al. | 73/863.91 |
| 4,857,471 A | * | 8/1989 | Salzman et al. | 436/43 |
| 4,908,320 A | * | 3/1990 | Zakowski et al. | 436/45 |
| 5,244,633 A | * | 9/1993 | Jakubowicz et al. | 422/64 |
| 5,271,896 A | | 12/1993 | Jakubowicz et al. | 422/63 |
| 5,316,726 A | * | 5/1994 | Babson et al. | 422/65 |
| 5,350,564 A | * | 9/1994 | Mazza et al. | 422/63 |
| 5,374,395 A | * | 12/1994 | Robinson et al. | 422/64 |
| 5,380,487 A | * | 1/1995 | Choperena et al. | 422/63 |
| 5,439,646 A | | 8/1995 | Tanimizu et al. | 422/64 |
| 5,585,068 A | * | 12/1996 | Panetz et al. | 422/100 |
| 5,658,799 A | | 8/1997 | Choperena et al. | 436/50 |
| 5,681,530 A | * | 10/1997 | Kuster et al. | 422/63 |
| 5,853,666 A | * | 12/1998 | Seaton et al. | 422/65 |
| 5,885,529 A | * | 3/1999 | Babson et al. | 422/65 |
| 5,985,672 A | * | 11/1999 | Kegelman et al. | 436/50 |
| 6,117,391 A | * | 9/2000 | Mootz et al. | 221/298 |

FOREIGN PATENT DOCUMENTS

| | | |
|---|---|---|
| DE | 39 34 890 A1 | 4/1990 |
| FI | 97913 B | 3/1997 |
| WO | 96/25712 A1 | 8/1996 |

* cited by examiner

*Primary Examiner*—Jill Warden
*Assistant Examiner*—Kathryn Bex
(74) *Attorney, Agent, or Firm*—Kubovcik & Kubovcik (57) ABSTRACT

A sample handling method, in which the information on the sample to be examined is transferred throughout the entire measuring process by transferring the sample cup. The sample cups are handled in two independently operating drums, in which case at least two different handling phases can be carried out simultaneously in the measuring device. The diagnostic measuring device comprises a cassette drum, on the circumference of which the sample cup cassettes containing sample cups have been placed. The sample cup is fed to the first handling drum, which is simultaneously an incubation drum. After that the sample cup is transferred to a second handling drum, where washing, drying, measuring and discharge of the sample cup are carried out. The drums have been placed near each other, overlapping so that the transfers of the sample cup can be performed directly from one drum to another by means of transfer plungers.

5 Claims, 7 Drawing Sheets

METHOD FOR HANDLING SAMPLES AND DIAGNOSTIC MEASURING DEVICE

BACKGROUND OF THE INVENTION

1. Field of the Invention

This invention relates to a diagnostic method and device.

An object of the invention is a method for handling samples, in which method a sample is brought to a measuring device, steps relating to the measuring process are carried out on the sample, and the sample is measured.

Diagnostic assay measurements are carried out in laboratories and hospitals, for example. Such analyses usually concern handling a patient's blood samples. The measuring methods and measuring devices that are used vary to a great extent. For example laboratories usually handle large amounts of samples. Particularly in screening tests, assay measurements are carried out so that the samples are brought together to efficient measuring devices, in which a large number of samples are measured at a time in one batch measurement. However, there is also a need for single measurements in hospitals, because the blood sample of a hospitalised patient should be analysed as quickly as possible. Screening test methods are not suitable for this.

Another object of the invention is a diagnostic measuring device. In particular, the object of the invention is a measuring device that enables patients' blood samples in hospitals to be tested as quickly as possible. One test result that is required quickly in hospitals is an analysis of whether there are signs of a recent myocardial infarction in the patient's blood sample. From the treatment point of view, it is of crucial importance that a diagnosis can be made at the earliest stage possible. In such case it is not possible to use the diagnostic analysis equipment used in screening tests, since they are used to measure a large number of samples at a time. It is not possible to use them for measuring single samples.

As the need for rapid measurement of single samples is known, attempts have been made to develop sample handling methods and measuring equipment in which the measurement of a single sample can be performed rapidly. However, a sample handling method or measuring device of this kind must also be such as to enable the addition of new samples to be measured throughout the measuring process without disturbing the steps for measuring the previous samples that have already been started.

2. Description of Related Art

One known diagnostic measuring device is presented in U.S. Pat. No. 5,635,364. In it, test tubes containing samples can be loaded on a rotating carousel-type drum around which there is a drum containing reagents. The samples are transferred to a separate analysis drum with a transfer pipette. However, the device is very large and elaborate.

Another automated random access analyser is presented in U.S. Pat. No. 5,679,309. This measuring device features three carousel-type drums. The drum in the middle is an analysis drum, on both sides of which there is a sample drum and a reactance drum. The samples and the reactants are transferred to the analysis drum by means of pipette-type transfer equipment.

The disadvantage of known sample handling methods and measuring devices is their elaborateness. It is possible in various methods and the equipment used in them to carry out random access to fetch a certain sample for measuring. They do not, however, comprise arrangements for effectively accelerating measurement. The slowness of sample handling methods and measuring devices is often caused by the fact that the steps relating to the measuring are carried out alternately in the process. Slow steps carried out in succession substantially increase the throughput time of the measuring process.

One problem in the known sample handling methods and measuring devices is the fact that the samples are usually transferred within the measuring process by means of pipettes. Such sample transferring members within a device are slow and elaborate. In addition, they are difficult to keep clean.

The purpose of this invention to obtain a quick and efficient sample handling method, most advantageously for hospital use. Another purpose of the invention is to obtain a simple and efficient measuring device without the disadvantages of the known devices presented above.

BRIEF SUMMARY OF THE INVENTION

It is characteristic of a sample handling method relating to the invention that the sample to be examined is transferred to the sample receptacle of the measuring device most advantageously by pipetting,     that the information on the sample to be examined is transferred in the measuring device throughout the entire measuring process by transferring the said sample receptacle,     and that the sample receptacle is handled in the measuring device in at least two independently operating handling members in such a way that at least two different handling phases are carried out simultaneously in the measuring device.

According to one preferred embodiment of the sample handling method relating to the invention     the sample receptacle used for measuring in the measuring device is transferred from the sample receptacle store into the actual measuring device,     within the measuring device, the sample receptacle is handled in at least two independently operating handling members,     and all the various phases of the measuring process are divided to be performed by the said independently operating handling members.

According to a second preferred embodiment of the sample handling method relating to the invention, in the measuring device, at least two phases of the measuring process are carried out simultaneously in the same independently operating handling member.

According to a third preferred embodiment of the sample handling method relating to the invention     in the measuring device, the sample receptacle to be used for measuring is selected from the independently operating sample receptacle store for the first independent handling device of the actual measuring device, in which handling device at least the dispensing and incubation of the sample are carried out,     and the sample receptacle is transferred from the first handling device to the second independently operating handling device in which the sample is at least measured and most advantageously the sample receptacle is also washed, dried and discharged.

It is characteristic of the measuring device relating to the invention, that the measuring device comprises members for transferring the sample receptacle within the measuring device, that the measuring device comprises at least two independently operating handling members and members for transferring the sample receptacle from one handling member to the second handling member, and that sample receptacle handling devices have been placed in conjunction with at least two independently operating handling members, with the aid of which handling devices at least two different handling phases can be carried out simultaneously on at least two sample receptacles.

According to one preferred embodiment of the measuring device relating to the invention the measuring device comprises an independently operating sample receptacle store and at least two independently operating handling members, the sample receptacle store has members for transferring a measuring receptacle of the desired type to the handling member of the actual measuring device, that the measuring device comprises at least two of the following sample receptacle handling stations: a sample dispensing station, an incubation station, a sample receptacle washing station, a sample receptacle drying station, a sample measuring station and a sample receptacle discharge station, and the said handling stations have been divided so as to be in conjunction with at least two independently operating handling members so that at least two different handling stations can be made to operate simultaneously.

According to a second preferred embodiment of the measuring device relating to the invention the sample receptacles are sample cups and the sample receptacle store is a cassette drum on the circumference of which the sample cup cassettes containing sample cups have been placed, the independently operating handling members are rotating drums, and the cassette drum, the first sample cup handling drum and the second sample cup handling drum have been placed in conjunction with each other partly on top of each other so that the sample cup can be transferred directly from one drum to another.

According to a third preferred embodiment of the measuring device relating to the invention the first sample cup handling drum is an incubation station, in conjunction with which a sample cup feeding station and a sample dispensing station have been placed, a sample receptacle washing station, a sample receptacle drying station, a sample measuring station and a sample receptacle discharge station have been placed in conjunction with the second sample cup handling drum, and both handling drums operate independently, so that at least one handling station of the first handling drum can be made to operate simultaneously with at least one handling station of the second handling drum.

According to a fourth preferred embodiment of the measuring device relating to the invention, at least two of the different handling stations that have been placed in conjunction with the second sample cup handling drum can be made to operate simultaneously.

According to a fifth preferred embodiment of the measuring device relating to the invention the axles of the cassette drum and sample cup handling drums of the measuring device are parallel, and the measuring device comprises a sample cup feeding device and, between the first and the second handling drum, a sample cup transfer device, which devices have transfer plungers parallel to the axles of the said drums.

BRIEF DESCRIPTION OF THE DRAWINGS

In the following, the invention is described by way of examples with reference to the accompanying drawings, in which.

DETAILED DESCRIPTION OF THE INVENTION

Figure 1:
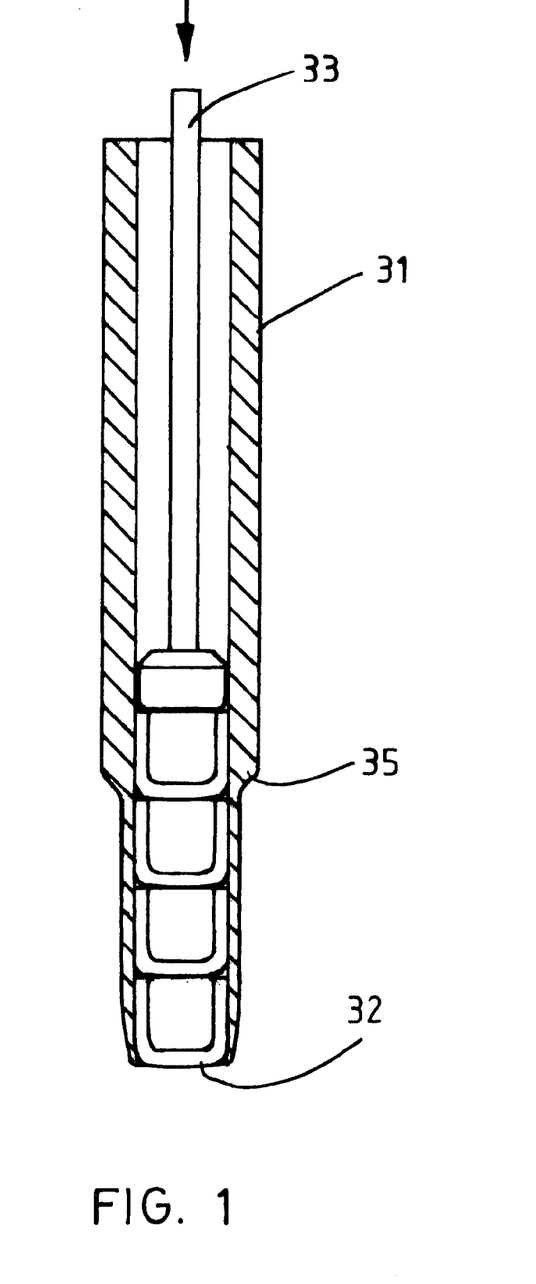
FIG. 1 shows a section of a sample cup cassette, seen from the side.

FIG. 1 shows a tubular sample cup cassette 31, in which single cup-like sample cups 32 have been placed one after another. The sample cup cassette 31 is placed in the cassette drum of the measuring device in an upright position so that the sample cups are in an upright position with the right side up. Depending on the method used in the measuring, the sample cups 32 can be completely empty cups or the walls of the sample cups can be coated with marker substances required in the measuring.

The mouth at the lower end of the sample cup cassette 31 in FIG. 1 is slightly tapered so that single sample cups 32 do not come out of the cassette 31 on their own. Discharge of the sample cups 32 from the cassette one at a time is effected by using a thrust plunger. FIG. 1 shows a diagrammatic view of the thrust plunger 33, which in the measuring device is situated in conjunction with the sample cassette drum, as presented in more detail in the subsequent figures.

On the outer surface of the sample cup cassette 31 there has been formed a tapered point 35 35, below which, at the lower end of the cassette 31, its outside diameter is smaller. The tapering has been made in order to enable the sample cup cassette 31 to be placed with the narrow end first in the correspondingly dimensioned holder of the sample cassette drum. This structure is presented in more detail in the next figure.

Figure 2:
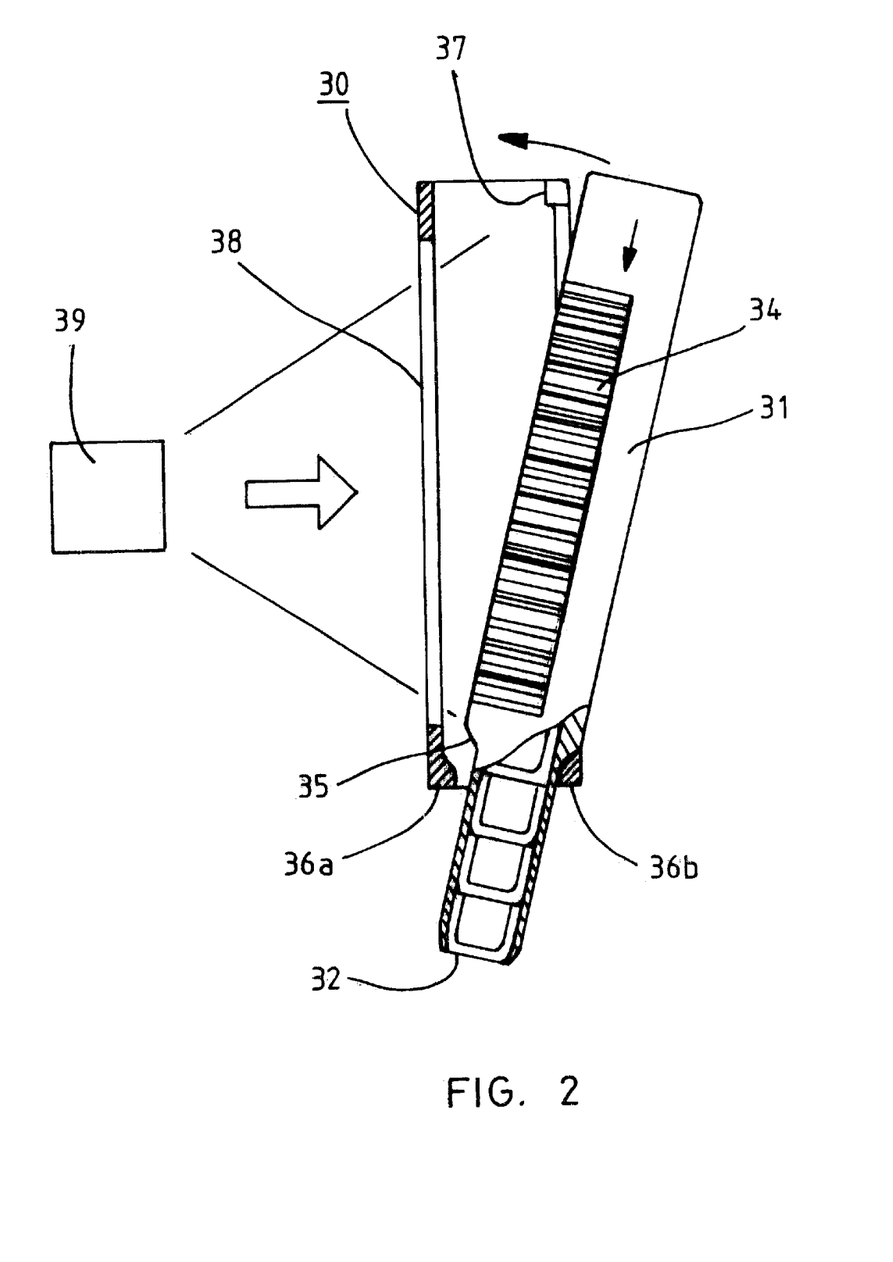
FIG. 2 shows the placing of a sample cup cassette in the cassette drum, seen from the side.

FIG. 2 shows diagrammatically the placing of the sample cup cassette 31 containing single sample cups 32 in the cassette drum 30 of the measuring device. FIG. 2 only shows that part of the cassette drum 30 that forms the holder of the sample cup cassette 31. The sample cup cassette 31 is put into its place in such a way that the narrower part below the tapered point 35 is pushed into the opening between the limiters 36a and 36b. The opening is suitably wide, so that the sample cup cassette 31 can also be pushed into place in a slightly inclined position, whereby the cassette 31 remains with its tapered point 35 resting on the limiters 36a and 36b. When the cassette 31 is pushed into an upright position, it is locked against the sill 37 of the holder, which sill is at the upper end of the cassette.

It can be seen in FIG. 2 that the sample cup cassette 31 is provided with a bar code 34, which enables the sample cups 32 in the cassette to be identified. To enable the bar code 34 to be read, an opening 38 has been made in the holder of the cassette drum 30 for the bar code reader 39, which is at the centre of the drum. Identification of the sample cups is necessary when there are sample cups that have been provided with different coatings in the cassette drum 30. This being the case, one sample cup cassette 31 always only contains sample cups 32 that are coated in the same way. Therefore, the sample cup 32 that is to be used is always identified by the bar code 34 of the sample cup cassette 31. The sample cups 32 themselves do not bear any identifying marks. However, empty and uncoated sample cups can also be used in the measuring device, in which case it is naturally not necessary to identify them.

Figure 3:
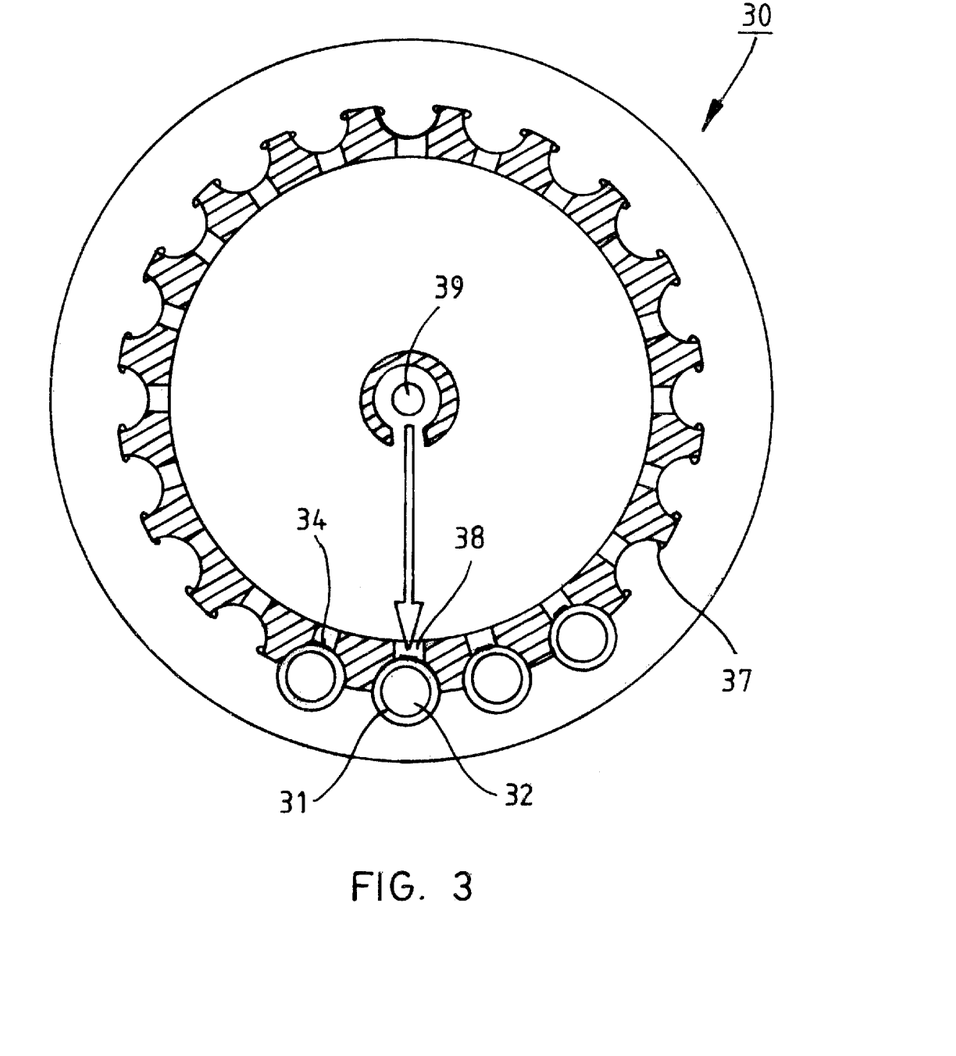
FIG. 3 shows a cassette drum, seen from above.

FIG. 3 shows the cassette drum 30 from above. It can be seen in the figure that the sample cup cassettes 31 have been placed on the circumference of the drum 30 in such a way that their bar codes 34 are facing the bar code reader 39 at the centre of the drum 30. In this way, the bar code reader 39 can read through the openings 38 the sample cup cassettes 31 that are on the drum 30. When the type of the next assay measurement to be carried out is known, the computer controlling the measuring device is instructed to fetch for use a sample cup 32 corresponding to the measuring method. Then the cassette drum 30 is rotated so that the sample cup cassette 32 provided with the corresponding identification moves to the feeding station of the cassette drum 30. After that a sample cup suitable for the measuring method used is taken from this sample cassette 31.

Figure 4:
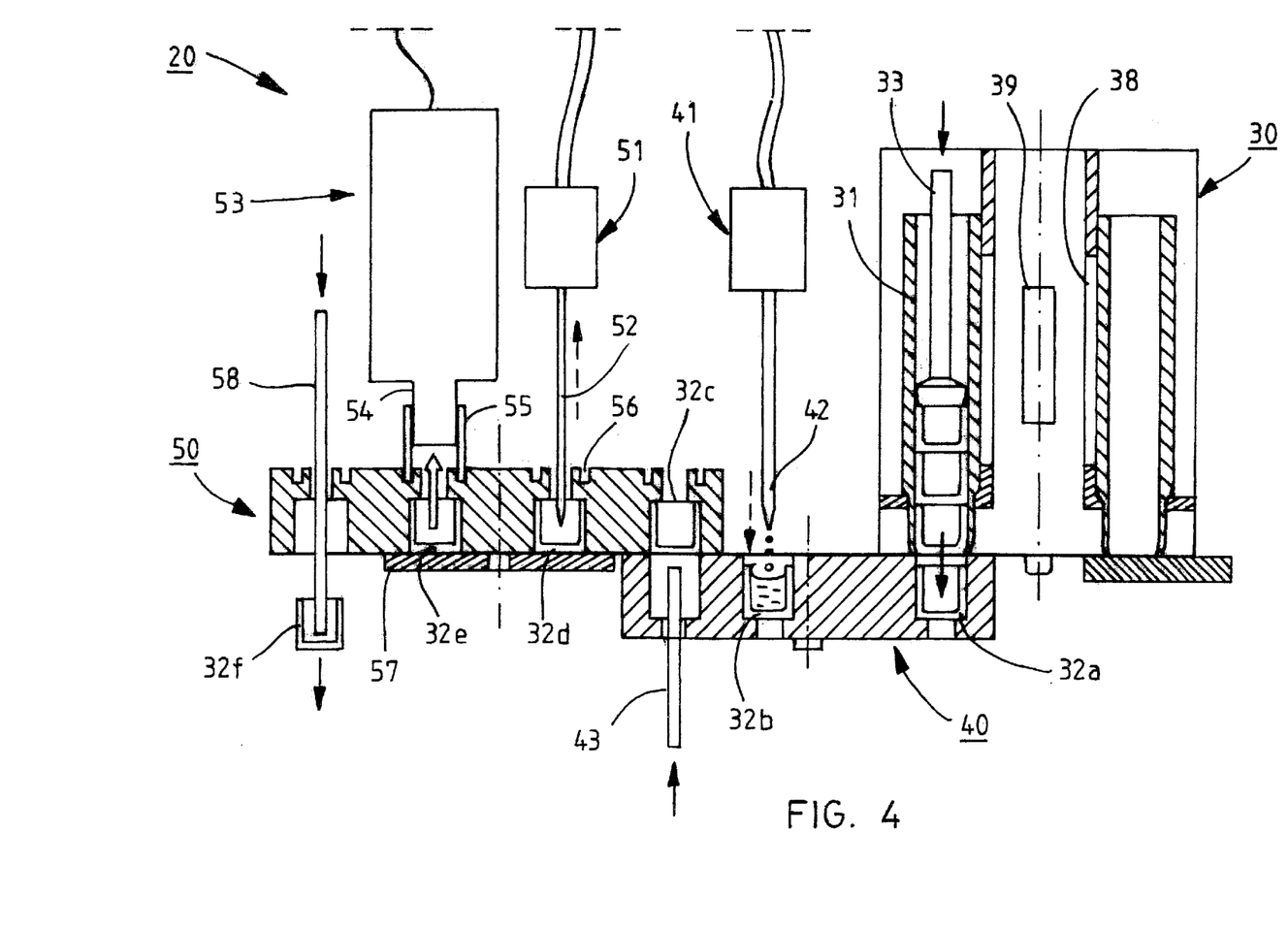
FIG. 4 shows a section of a diagrammatic view of the equipment arrangement, seen from the side.

FIG. 4 shows a diagrammatic view of the structure of the measuring device 20 and a diagrammatic view of the passage of a single sample cup 32 in the measuring device 20 by way of one example. For the sake of clarity, the measuring device 20 has therefore been simplified, and neither do the sections of the various drums 30, 40 and 50 of the measuring device 20 represent a real sectional plane. The passage of a sample cup 32 in the measuring device 20 may, however, vary considerably, since the movements and operation of the drums 30, 40 and 50 can be changed. In this case the passage of the sample cup 32 in the measuring device 20 differs from that presented in FIG. 4.

FIG. 4 shows on the right the cassette drum 30 of the measuring device 20, in which cassette drum the sample cup cassettes 31 are placed. To measure a new sample, the cassette drum 30 is rotated so that the desired sample cup cassette 31 moves to the feeding point for the sample cups 32. The bar code reader 39 checks the bar code of the sample cup cassette 31 to ensure that the cassette that is at the feeding point contains sample cups 32 meant precisely for measuring this sample. After that a new sample cup 32a is taken for use from the sample cup cassette 31 in such a way that the plunger 33, which is in conjunction with the drum 30, presses the sample cups in the cassette 31 downwards. Then the sample cup 32a that is lowest in the cassette 31 is fed into the sample cup station of the first handling drum 40 of the measuring device 20.

In this exemplary embodiment, the first handling drum 40 is called an incubator drum, since only the sample dispensing and the incubation and shaking phases are carried out there. However, it is also possible that the tasks to be performed are distributed in a completely different way between the various handling drums 40 and 50 of the measuring device 20.

After a new sample cup 32a has been fed to the first handling drum 40, i.e. to the incubator drum 40, the drum 40 rotates so that the sample cup 32a moves to the dispensing station, to the sample dispensing device 41. In FIG. 4, the sample cup that has moved to the dispensing device 41 is marked with reference number 32b. When the dispenser probe 42 of the dispensing device 41 has dispensed the liquid sample solution into the sample cup 32b, the reciprocating vibratory motion of the incubator drum 40 is started in order to incubate the sample. Thus the incubator drum 40 is simultaneously a vibrator. In the incubation phase the sample is shaken, for example, for 15 minutes at a temperature of 36° C.

After the incubation of the sample has been carried out, the vibratory motion of the incubator drum 40 is stopped. After that the drum 40 will rotate to a position where the sample cup containing the incubated sample solution is transferred to the second handling drum 50 of the measuring device 20. FIG. 4 shows the plunger 43 situated at this point of the measuring device 20, which plunger lifts the sample cup upwards to the handling drum 50. The sample cup that has been transferred to the handling drum 50 is marked with reference number 32c.

In this exemplary embodiment, all the other preparatory phases required for measuring, such as washing and drying of the sample cup 32, sample measuring and discharging of the sample cup 32, have been programmed to be carried out by the second handling drum 50. However, the tasks can also be divided in a different way between the handling drums 40 and 50. It is advantageous to divide the most time-consuming phases relating to measuring to different drums 40 and 50. Because different work phases can be carried out independently and simultaneously on both handling drums 40 and 50, the entire measuring process can be carried out in the shortest time possible. Incubation is the step that usually takes the most time, so the division of tasks presented in this example is advantageous. This is also the reason why the first handling drum 40 can take approximately three times as many sample cups 32 to be incubated as the second handling drum 50, where the work phases to be carried out take considerably less time.

After this, in FIG. 4, the second handling drum 50 rotates so that the sample cup moves to the washing station 51. The sample cup that is at the washing station 51 is marked with reference number 32d. At the washing station 51 the sample solution is discharged from the sample cup 32d, and the sample cup 32d is washed for example, for 30 seconds. After that the sample cup 32d is emptied and dried. At the washing station 51, the emptying of the sample cup 32d and the feeding and discharge of detergent are carried out by means of pipettes 52. In practice, the feeding and discharge pipettes are most advantageously separate, but for the sake of simplicity, FIG. 4 shows only one pipette 52 of the washing station 51. The sample cup drying station is also most advantageously a separate station, as is shown in the next figure, but it is not shown in FIG. 4. After the sample cup 32d has been washed and dried, measurement is carried out.

In the example shown in FIG. 4 the measuring is carried out on the coating layer on the inside of a dry sample cup. Alternatively however, sample cups that contain fluid can also be measured in the measuring device shown in FIG. 4. Then the reagent solution is added to the sample cup before measuring. The reagent adding station can then be for example, at or next to the drying station marked with reference number 59 in (see FIG. 6).

For measuring, the handling drum 50 of the measuring device 20 rotates so that the sample cup moves to the measuring station 53. The sample cup at the measuring station 53 is marked with reference number 32e. During measuring, the measuring head 54 of the measuring station 53 is above the sample cup 32e and the light shield 55 of the measuring head 54 is pressed down against the surface of the handling drum 50. FIG. 4 also shows that to ensure impermeability to light, an annular groove 56 has been formed on the surface of the handling drum 50 at each sample cup.

After the measurement has been carried out, the handling drum 50 of the measuring device 20 rotates again. Now the measured sample cup comes to the discharge station. The sample cup to be discharged is marked in FIG. 4 with reference number 32f. It can be seen in FIG. 4 that there is an opening in the sample cup discharge station, in the bottom plate 57 under the handling drum 50, whereby the sample cup 32f is able to fall downwards. The downward movement of the plunger 58 ensures that the sample cup 32f has with certainty been discharged from the measuring device 20.

Figure 5:
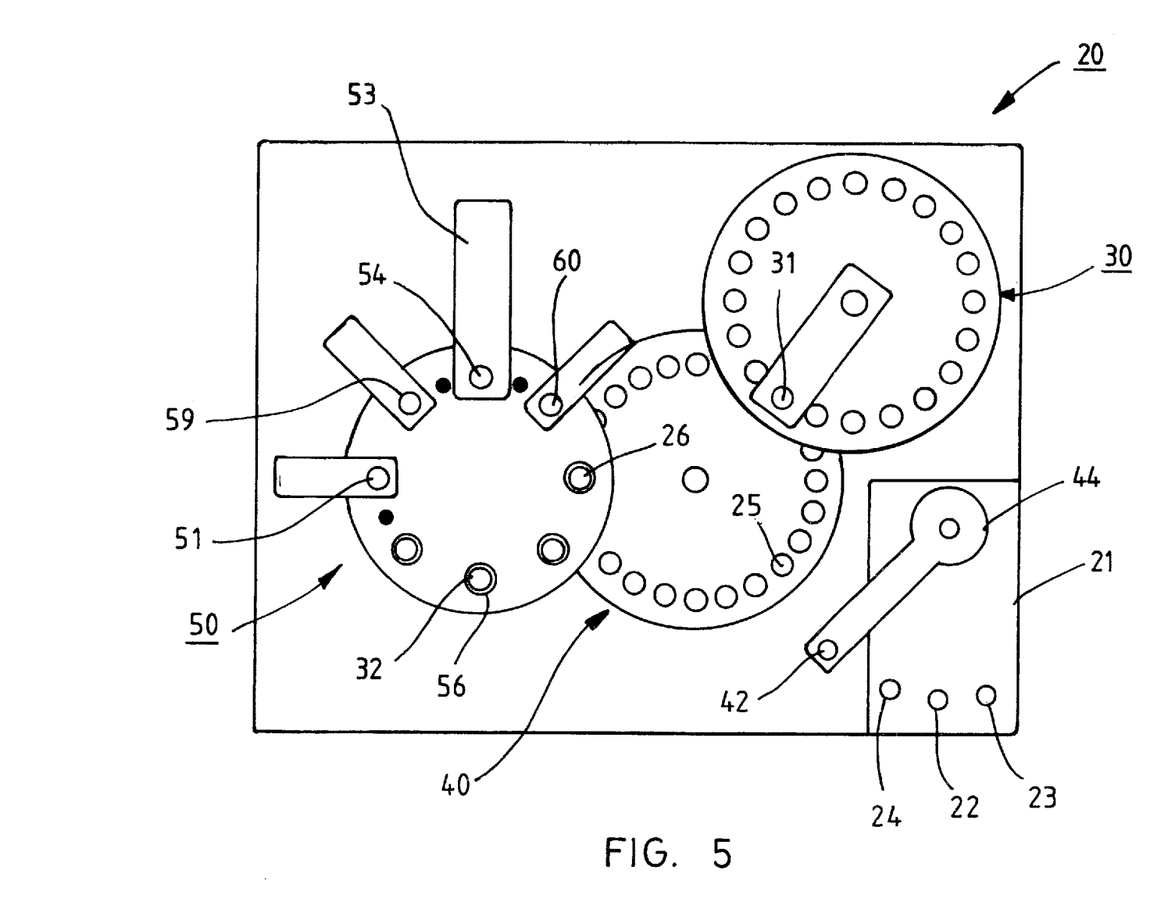
FIG. 5 shows a diagrammatic view of the equipment arrangement, seen from above.

FIG. 5 shows the equipment arrangement of the measuring device 20, seen from above. The sample receptacle containing the sample to be measured, which sample receptacle is usually a test tube, is brought into the pipetting unit 21 and placed in the sample station 22, which in this example is called a test tube station. In the pipetting unit 21, beside the test tube station 22, there is a sample diluting station 23, and at the opposite side of the test tube station 22, a pipette washing point 24. The pipette 42 of the dispensing device 41 of the pipetting unit 21 is used to perform dispensing of the sample into the sample cup, and possibly dilution.

Before starting measurement, the identification code or number of the test tube that contains the sample to be measured is given to the measuring device 20. The identification can also be read from the bar code of the test tube. When the test tube has been placed in the test tube station 22, the measuring method is selected. If more than one test is to be carried out, the control device is instructed to fetch a corresponding number of sample cups for the measurements.

When the measurement is started, the cassette drum 30 is turned to a position where a sample cup cassette 31 containing sample cups 32 suited precisely for this measurement at the sample cup feeding station. After that the sample cup 32 is fed to the first handling rum 40, i.e. to the incubator drum. Immediately after that the incubator drum 40 rotates and moves this sample cup to the dispensing station 25. If various sample cups have been taken onto the drum 40, they move one by one to the dispensing station 25.

In FIG. 5 the various work phases of measurement proceed so that the dispensing pipette 42 of the dispensing device 41 takes sample solution from the test tube 22 and dispenses 10 μl of the solution and 20 μl of the buffer solution into the first sample cup in the dispensing station 25. Before dispensing, the pipetting tip already contains the buffer, which is separated from the sample by a small air gap in the pipetting tip. Correspondingly, sample solution and buffer solution are also dispensed into the other sample cups which are brought in their turn into the dispensing station 25.

After dispensing, the reciprocating vibratory motion of the incubator drum 40 is started in order to incubate the samples. In the incubation phase, the samples are shaken for example, at a temperature of 36° C. for 15 minutes. After incubation, the incubation drum 40 rotates to a position where the first sample cup moves to the elevator station 26, where the sample cup is lifted to the handling drum 50. Other sample cups can also be lifted to the handling drum 50 in a similar manner already before washing, drying and measuring are started.

After the sample cups have been lifted to the second handling drum 50, the handling drum 50 is rotated so that the first sample cup moves to the washing station 51. The sample cup is washed for 30 seconds, for example. After washing, the handling drum 50 rotates again so that the washed sample cup moves to the drying station 59 and the next sample cup to the washing station 51. The washing of the first sample cup and the drying of the second sample cup can then be carried out simultaneously, and they both take 30 seconds in this case.

After drying, the second handling drum 50 rotates again so that the dried sample cup moves to the measuring head 54 of the measuring station 53. Correspondingly, the second sample cup that has been in the washing station 51 moves into the drying station 59 and the third sample cup into the washing station 51. If the sample cup measurement can be carried out in the same time as washing and drying, the handling drum 50 can be rotated so that the sample cups proceed at regular intervals from one handling phase to another. Then the measuring of the first sample cup, the drying of the second sample cup and the washing of the third sample cup occur simultaneously. In this way each sample cup is washed, dried and measured in turn and discharged from the discharge station 60 after measurement. The concentration and measuring results of each sample cup are shown on the display and also printed on paper.

It can be noticed from the description of the measuring process presented above that the sample cup 32 proceeds through the entire measuring process, but all the different work phases are not by any means carried out successively in turn, as in known measuring devices. According to the invention, the measuring process can be carried out substantially faster when, besides the simultaneous work phases carried out at different handling drums 40 and 50, different work phases are also carried out simultaneously at the same handling drum 50. In other words, in the example presented, the division of tasks is such that in the measuring device 20 relating to the invention, all of the subsequent work phases are carried out simultaneously. Firstly, incubation is carried out on some of the sample cups 32 at the first handling drum 40, and sample cups 32 which are further on in the process, at different phases, are washed, dried, measured and discharged simultaneously at the second handling drum 50. It is clear that this procedure substantially accelerates the measuring process and the throughput of the sample cup 32 in the measuring device 20.

However, it is not always possible to use the second handling drum 50 in the way presented above. For example, there may be some reasons concerning the handling of the sample, which dictate that only one sample cup can be taken at a time from the incubator drum 40 to the handling drum 50, for example. Therefore the order of the various operations can be modified as necessary. The number of sample cups that can be taken to the second handling drum 50 at a time is also limited. For example, in FIG. 5, the handling drum 50 can clearly take fewer sample cups than the incubator drum 40.

FIG. 5 also shows a detail presented in the previous figure. On the surface of the handling drum 50, around the sample cups 32 annular grooves 56 have been formed, into which the light shield that is in conjunction with the measuring head 54 is pressed for the duration of the measurement thus ensuring that the space between the measuring head 54 and the sample cup 32 is impermeable to light.

Figure 6:
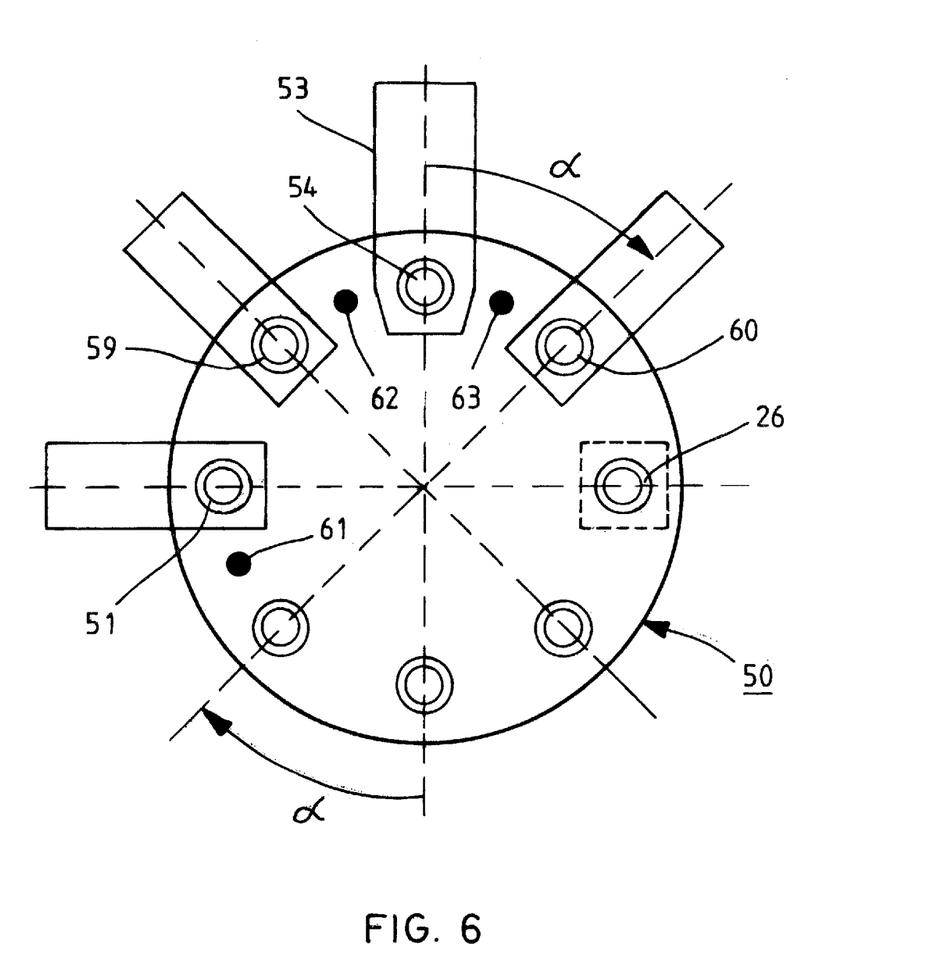
FIG. 6 shows a diagrammatic view of the sample cup handling drum, seen from above.

FIG. 6 shows the second handling drum 50, seen from above. The sample cups are lifted to the handling drum 50 at the elevator station 26. FIG. 6 also shows the location of the washing station 51, the drying station 59, the measuring head 54 and the discharge station 60 in relation to the handling drum 50. In the example in FIG. 6, the handling drum 50 has eight places for sample cups, the places being grouped in a regular manner. This means that the angle of rotation of the handling drum 50 is always 45° as the sample cup proceeds from one handling phase to another.

However, the other handling stations 61, 62 and 63, which have been placed between the sample cup handling stations, can also be seen in FIG. 6. These handling stations are the washing head washing station 61, the reference well 62 and the opening 63 for the probe. They are meant to be used as necessary between the handling phases described above, as shown in the next figure.

Figure 7:
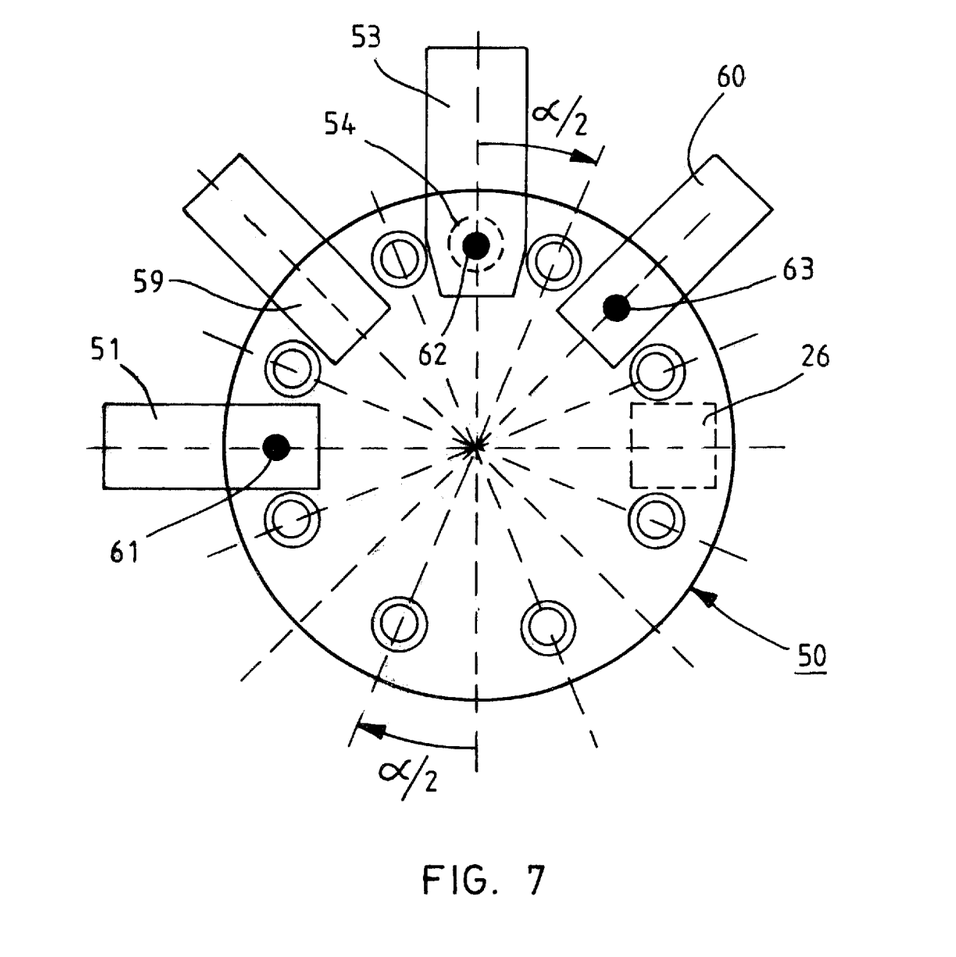
FIG. 7 corresponds to FIG. 6 and shows the sample cup handling drum in another position.

It can be seen in FIG. 7 that the handling drum 50 has been turned by an angle of /2, i.e. by 22.5°, in which case the washing head washing station 61 is at the washing station 51, the reference well 62 is at the measuring head 54 of the measuring station 53 and the opening 63 is at the probe of the discharge station 60. This intermediate position of the handling drum 50 can be used at any time to wash the washing heads of the washing station 51 or to verify the reference standard. The opening 63 is included in the embodiment presented in this example because the downward movement of the probe of the discharge station 60 occurs simultaneously with the movement of the measuring head 54 towards the sample cup.

It is essential for the measuring device 20 presented above that the cassette drum 30 containing sample cups, the incubator drum 40 provided with a motion, and the sample handling drum 50 can each be rotated separately in either direction. This means that each of these drums 30, 40 and 50 can operate independently and each perform their own task irrespective of one another. This enables the first samples to be measured and the next samples to be incubated simultaneously, for example. However, when the sample cup 32 moves from one drum to another, the movement of these drums must naturally be co-ordinated and stopped for a while in a position where the sample cup can be moved.

In the embodiment of the measuring device 20 presented above the members used to transfer and handle the sample cups 32 are drums 30, 40 and 50. These members can, however, be made so that they also move in any direction in the xy-coordinate system i.e. in the xy-plane. In this way, too, the movements of the sample cup handling members can be co-ordinated so that the sample cup can move from the cassette store to the incubator and from there further to the handling member and to the measuring station. In this case, too, it is essential that the handling members can operate independently and carry out different operations simultaneously.

The measuring device 20 relating to the invention can be made to be completely computer-controlled and thus automatic. The user of the device only needs to place a sample receptacle containing a sample in the sample station 22. In this example the sample is in a test tube that is brought to the test tube station 22, but the sample may also be in a different receptacle. The control devices of the measuring device 20 are not presented in the drawings. The measuring device 20 can also be made to be independent and continuously operating in such a way that a sample feeding device is connected to it, which device feeds test tubes containing samples or other sample receptacles to the sample station 22 of the measuring device.

It is obvious to a person skilled in the art that the different embodiments of the invention may vary within the scope of the claims presented below.

What is claimed is:

1. A sample handling method comprising the steps of:
   (1) providing a sample cassette drum for holding a plurality of sample cup cassettes around the circumference thereof, each sample cup cassette holding a plurality of sample cups, and said sample cassette drum being arranged to rotate around a vertical axis;
   (2) providing first and second handling drums, each handling drum having a plurality of holding means provided around the circumference thereof for holding sample cups and being arranged to rotate around a vertical axis, said sample cassette drum and said first and second handling drums being arranged such that a sample cup can be vertically transferred from said sample cassette drum into one of said plurality of holding means of said first handling drum and can be vertically transferred from said holding means of said first handling drum into one of said plurality of holding means of said second handling drum;
   (3) selecting a sample cup from one of said plurality of sample cup cassettes and transferring said sample cup in a vertical direction to one of said plurality of holding means of said first handling drum;
   (4) rotating said first handling drum to a position where said sample cup is adjacent a sample dispensing means;
   (5) dispensing a sample to be examined from said sample dispensing means into said sample cup;
   (6) subjecting said sample in said sample cup in said first handling drum to at least one analysis step;
   (7) rotating said first handling drum to a position where said sample cup is located directly underneath one of said plurality of holding means of said second handling drum;
   (8) transferring said sample cup in a vertical direction to said holding means of said second handling drum;
   (9) rotating said second handling drum to a position where said sample cup is adjacent to a station for performing an analysis step;
   (10) subjecting said sample in said sample cup in said second handling drum to at least one additional analysis step at said station;
   (11) transferring another sample cup from said one of said plurality of sample cup cassettes in a vertical direction to another of said plurality of holding means of said first handling drum;
   (12) repeating steps (4)–(10) with said another sample cup;
   (12) optionally repeating steps (11)–(12); and
   (13) removing said samples and sample cups from said second handling drum;
   wherein at least two different analysis steps are carried out simultaneously in said first and second handling drums.

2. A sample handling method as recited in claim 1, wherein a sample to be examined is dispensed from said sample dispensing means to said sample cup by pipetting.

3. A sample handling method as recited in claim 1, wherein at least two analysis steps are carried out simultaneously in said first handling drum or in said second handling drum.

4. A sample handling method as recited in claim 1, wherein said at least one analysis step carried out in said first handling drum is selected from the group consisting of incubating and shaking.

5. A sample handling method as recited in claim 1, wherein said at least one analysis step carried out in said second handling drum is selected from the group consisting of washing, separation, drying and measuring.

* * * * *

UNITED STATES PATENT AND TRADEMARK OFFICE
CERTIFICATE OF CORRECTION

PATENT NO.    : 6,551,833 B1                                          Page 1 of 1
DATED         : April 22, 2003
INVENTOR(S)   : Kauko Lehtinen et al.

It is certified that error appears in the above-identified patent and that said Letters Patent is hereby corrected as shown below:

Title page,
Item [56], References Cited, U.S. PATENT DOCUMENTS, insert:
-- 4,906,433 A       03/1990      Minekane              422/64
   5,441,891 A       08/1995      Burkovich et al.      436/48
   5,456,883 A       10/1995      Burkovich et al.      422/64 --
FOREIGN PATENT DOCUMENTS, insert:
-- EP 0 571 032 A1   11/1993
   EP 0 657 215 A1   06/1995
   JP 10-332706 A    12/1998 --
Following FOREIGN PATENT DOCUMENTS Listings, insert:
-- OTHER PUBLICATIONS
Smith, J., et al. "Abbott AxSYM Random and Continuous Access Immumoassay System for Improved Workflow in the Clinical Laboratory" *Clinical Chemistry*; American Association for Clinical Chemistry; vol. 39, no. 10, 1993. --

Signed and Sealed this

Twenty-sixth Day of August, 2003

JAMES E. ROGAN
*Director of the United States Patent and Trademark Office*